United States Patent
Aboul-Hosn et al.

(10) Patent No.: US 6,295,877 B1
(45) Date of Patent: Oct. 2, 2001

(54) PRESSURE SENSING CANNULA

(75) Inventors: Walid N. Aboul-Hosn; William R. Kanz; Kelly J. McCrystle, all of Sacramento, CA (US); Desmond P. O'Connell, Seattle, WA (US)

(73) Assignee: A-Med Systems, Inc., West Sacramento, CA (US)

( * ) Notice: Subject to any disclaimer, the term of this patent is extended or adjusted under 35 U.S.C. 154(b) by 0 days.

(21) Appl. No.: 09/280,970

(22) Filed: Mar. 30, 1999

(51) Int. Cl.[7] .................................................. G01L 7/00
(52) U.S. Cl. .................................................. 73/756
(58) Field of Search .............................. 604/4, 5, 34, 6, 604/153; 73/714, 756

(56) References Cited

U.S. PATENT DOCUMENTS

| | | |
|---|---|---|
| 4,508,535 | 4/1985 | Joh et al. . |
| 5,435,308 | 7/1995 | Gallup et al. . |
| 5,755,687 | 5/1998 | Donlon . |
| 5,797,948 | 8/1998 | Dunham . |
| 5,814,004 * | 9/1998 | Tamari ...................................... 604/4 |

FOREIGN PATENT DOCUMENTS 0 280 225   8/1998   (EP) .

* cited by examiner

Primary Examiner—William Oen
(74) Attorney, Agent, or Firm—Jonathan Stangler (57) ABSTRACT

A cannula is provided with one or more pressure transducers for measuring fluid pressure interiorly or exteriorly of the cannula. The pressure transducers may be mounted integrally with the tubular wall defining the main lumen of the cannula, or they may comprise differential pressure transducers mounted in dedicated lumens in communication with the main lumen. The pressure measurements from the transducers is used to determine fluid flow rate.

12 Claims, 9 Drawing Sheets

PRESSURE SENSING CANNULA

BACKGROUND OF THE INVENTION

1. Field of the Invention

The present invention relates to cannulas used in surgical applications, and more particularly, to a cannula equipped with a pressure/flow rate transducer.

2. Description of Related Art

In medical applications and specifically in surgery, the list of uses for cannulas is exhaustive. One application involves the augmenting or supplementing of pulmonary blood flow through the beating heart during cardiosurgery by use of one or more cannulas involved in the intake and return of blood into the circulatory system. The cannulas interface between the patient's circulatory system and the mechanical pumps that power the augmentation procedure. Such an application is described in co-pending PCT Application no. PCT/US97/18674 entitled "Single Port Cardiac Support Apparatus", filed Oct. 14, 1997 and incorporated herein by reference in its entirety.

When performing cardiac surgery cannulas are placed within the patient's blood stream and used for inflow and outflow of blood or other fluids. If the operator wishes to determine the rate of fluid flow, either a catheter with appropriate sensors must also be placed in the patient's blood stream, or other sensors such as an external ultrasonic sensor as disclosed in U.S. Pat. No. 5,179,862 are used. A shortcoming of ultrasonic systems such as that described in U.S. Pat. No. 5,179,862 is that they require significant monitoring. Ultrasonic sensors also require that tubing of a specific diameter be used, thereby adding to the cost and complexity of the surgical procedure. Additionally, ultrasonic sensors are expensive and non-disposable, thereby adding to the cost of the surgical procedure.

Another method to measure flow rate is through the use of a thermodilution catheter. Thermodilution catheters require the infusion of a solution, typically saline, of a known temperature, with a distally disposed thermistor measuring the temperature change to determine the flow rate. This method is also expensive, increasing the cost of the surgical procedure. A second problem with using flow-sensing catheters, such as thermodilution catheters, is that they require the operator to place more incisions within the patient. The catheters must be placed so that they do not interfere with the inflow or out flow of the cannula. Visual markers along the length of the cannula may also be used to determine location, the greater the number of markers the more accurate the placement at the expense of quick readings due to the greater number of markings.

SUMMARY OF THE INVENTION

The present invention overcomes the deficiencies of the prior art by providing a cannula assembly having one or more pressure transducers coupled to a main lumen thereof. In accordance with a first embodiment, the pressure transducers are attached to the substantially tubular wall defining the main lumen.

In accordance with a second embodiment, a partial occlusion is provided in the cannula to increase the pressure drop across the main lumen. In this manner transducer signal is increased, and an improved differential pressure measurement signal achieved.

In accordance with a third embodiment of the invention, one or more pressure transducers are used in conjunction with a pair of coaxial cannulas for measuring pressure.

In accordance with at fourth embodiment of the invention, a differential pressure transducer is used, the differential pressure transducer being mounted in a dedicated secondary lumen in communication with the first lumen.

In accordance with a fifth embodiment of the invention, the secondary lumen housing the differential pressure transducer is disposed across a knee formed in the cannula to augment pressure measurement. Partial occlusions may also be provided for this purpose.

In accordance with a sixth embodiment of the invention, the secondary lumen housing the differential pressure transducer is formed integrally with the tubular wall defining the main lumen.

In accordance with a seventh embodiment of the invention, a soft, flexible tapered tip is provided at the distal end of the cannula. Such a configuration allows for easier negotiation through the patient's body during surgical procedure.

In accordance with an eighth embodiment of the invention, an inflatable balloon is provided at the distal end of the cannula. The inflatable balloon aids in transporting the cannula to the desired destination.

In accordance with a ninth embodiment of the invention, a guide wire lumen is provided for supporting a guide wire in the cannula. The guide wire is used as a predecessor step in the insertion of the cannula.

In accordance with a tenth embodiment of the invention, a light guide is supported in the cannula. The light guide conveys light to a predetermined portion of the cannula to thereby aid in the visualization and location of the cannula during the surgical procedure.

The invention realizes various advantages over the prior art, including a reduction in the number of incisions that a surgeon must make in performing surgical procedures, along with a reduction in the amount of foreign material introduced into the patient's body, while providing safe, rapid, accurate and cost-effective fluid flow rate measurements.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein.

DETAILED DESCRIPTION OF THE PREFERRED EMBODIMENTS

In accordance with the invention, a cannula comprising a substantially tubular, semi-flexible material adapted for fluid transport while inserted in a patient's body is provided with one or more pressure transducers which are fixedly or adjustably supported in the cannula. The pressure transducers are disposed internally or externally of the cannula and are used to provide a measurement of the rate of fluid flow. In the internal configuration, the rate of fluid flow within the cannula is measured. In the external configuration, the rate of fluid flow outside the cannula is measured. The cannula can also be adapted to support a guide wire to aid the operator in its insertion through the patient's body, and/or a light source to provide a visual reference during the insertion procedure. It is to be understood that the use of the term "cannula" is intended to encompass cannulas, catheters, and any related devices having similar application.

Figure 1:
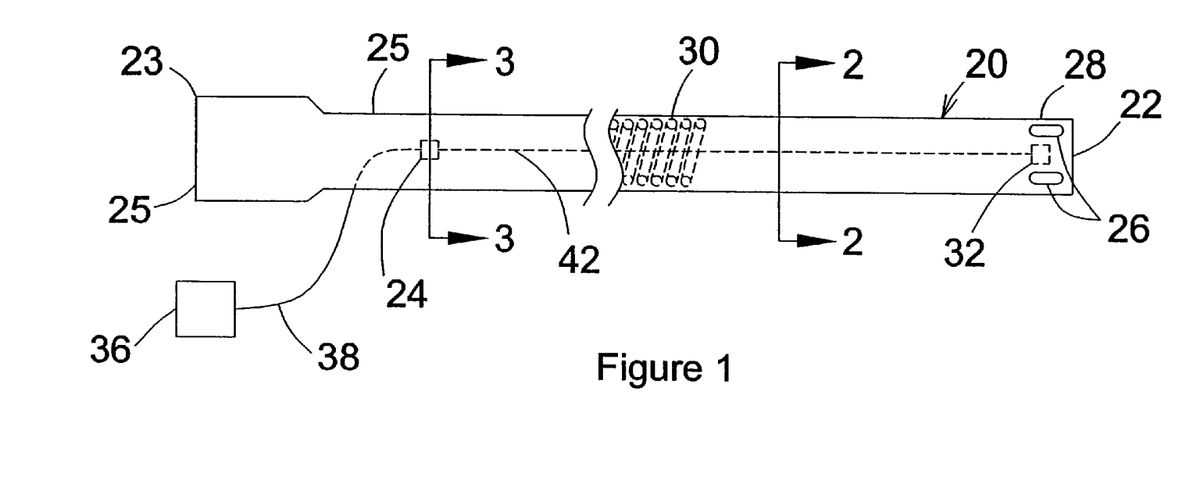
FIG. 1 is a schematic side view of a first embodiment of the invention.
Figure 2:
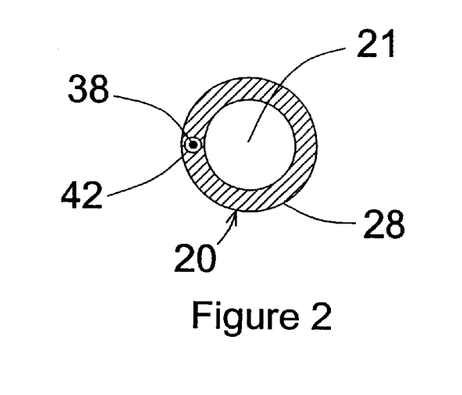
FIG. 2 is a schematic cross-sectional view taken along line 2—2 of FIG. 1.
Figure 3:
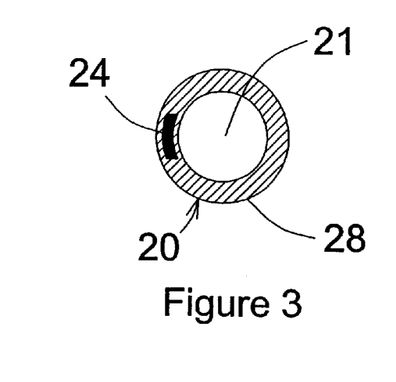
FIG. 3 is a schematic cross-sectional view taken along line 3—3 of FIG. 1.

An exemplary arrangement in accordance with a first embodiment of the invention is shown FIGS. 1–3. Cannula 20 comprises a substantially cylindrical structure having a wall 28 defining a main lumen 21. Wall 28 can be formed of materials ranging from rigid to flexible, and in the preferred embodiment comprises a semi-rigid transparent material such as polyurethane, silicone rubber or other material. Lumens other than main lumen 21 may also be provided, as described below. The cannula may also be formed from vinyl plastisol. To form a cannula of vinyl plastisol, a mandrel is dipped into liquid vinyl plastisol and heated. Wire is then wrapped around the mandrel and first formed layer. The mandrel is then dipped again encasing the wire, and then heated. The mandrel is then removed. Lumens and transducers may be formed within the wall of the cannula during the dipping process.

To lend structural support for the thin wall which allows maximum flow with minimal insertion damage, spiraling wire 30 is provided for reinforcement and is either molded into the wall 28 or is otherwise supported therein, and extends either partially or fully across the length of the cannula 20. Wire 30 facilitates handling of the cannula 20 and reduces the possibility of cannula 20 collapsing or being pinched shut and thus closing off the flow of fluid to or from the patient. Other ways of reinforcing the tubular body of cannula 20 are known in the art and will adapt equally well to the present invention. In addition, no reinforcement may be needed if the cannula material is sufficiently rigid or if sufficient fluid flow is present within the cannula.

A connector 23 is provided at the proximal 25 end of cannula 20. Connector 23 is suitably sized to interface with various surgical instruments, including but not limited to a reverse flow pump or fluid conduits leading thereto (not shown). Cannula 20 may also have one or more holes 26 located adjacent to distal tip 22 to facilitate fluid flow therethrough. Cannula 20 may be one of two complementary cannulas used in a surgical procedure, one for intake and the other for removal of blood or other bio-compatible fluid from the patient's body. Alternatively, cannula 20 may comprise a component of a co-axial, single port device in which cannula 20 is surrounded by a second, larger conduit, with cannula 20 for example operating to intake blood from the patient towards a pump system and the conduit operating to replace the blood from the pump system back into the patient for augmentation of blood flow during beating heart surgery as described in the co-pending PCT Application No. PCT/US97/18674 mentioned above.

In order to provide real time fluid flow information in accordance with the present invention, a pair of pressure transducers 24, 32 are provided at two separate locations as illustrated in FIG. 1. Pressure transducers 24, 32 are of the type known in the art and each comprises for instance a piezo-electric crystal housed in an integrated circuit (IC) chip (not shown). The crystal configuration is designed to be pressure sensitive, generating an electrical signal in proportion to the amount of pressure experienced.

The principle governing the relationship between fluid flow and pressure is defined by Bernoulli's equation, herein solved for flow rate V and is determined by $$V = \sqrt{\frac{\Delta P \cdot 2d \cdot a^2}{f \cdot L \cdot \rho}}$$

where $\Delta P$ is the measured difference in pressure, d is the internal diameter of the lumen, $\alpha$ is the area of the lumen, $f$ is a frictional factor of the lumen material, L is the lumen length over which the pressure measurement is conducted, and $\rho$ is a measurable constant representative of the density of the fluid. The flow rate information can be used for a variety of purposes, including monitoring the patient's condition and controlling the fluid pump used during the procedure.

In the preferred embodiment, transducers 24, 32 are imbedded in the wall 28, which is formed for instance by application of successive layers of laminate and interjecting the transducers therebetween during the layering process. Depending on at what stage in the layering process the transducers 24, 32 are put in place in the wall 28, their proximity to the interior of the cannula 20 or its exterior can be controlled in order to optimize measurement of cannula interior or exterior pressure. From the interior pressure measurements, a determination of flow rate within main lumen 21 can be made using the known diameter of the main lumen 21. Similarly, from the exterior pressure measurements, flow rate of exterior fluid—for example, blood—can be measured if the diameter of the blood channel, such as the artery, is known, or the cannula can be calibrated with thermodilution catheters which assume the diameter of the vessel or artery they are placed within.

In the FIG. 1 exemplary arrangement, pressure transducer 32 is disposed at a location near the distal tip 22 of cannula 20, while pressure transducer 24 may be disposed anywhere along the length of cannula 20 between pressure transducer 32 and proximal end 25. It is also contemplated that the pressure transducers 24, 32 may be detachably disposed in dedicated secondary lumens formed in or along tubular wall 28, the dedicated secondary lumen extending to the proximal end 25 and supporting any electrical cables connected to the pressure transducers 24, 32. In the detachable arrangement, the location of pressure transducers 24, 32 in the cannula 20 can be adjusted to suit the particular application, such that one transducer can be disposed within one chamber of the heart while the other is at a different of portion of the heart to thereby provide a pressure/flow rate measurement of a predetermined portion of the patient's body, for example flow into the heart from a designated blood vessel. Such an application is shown if FIG. 4.

Figure 4:
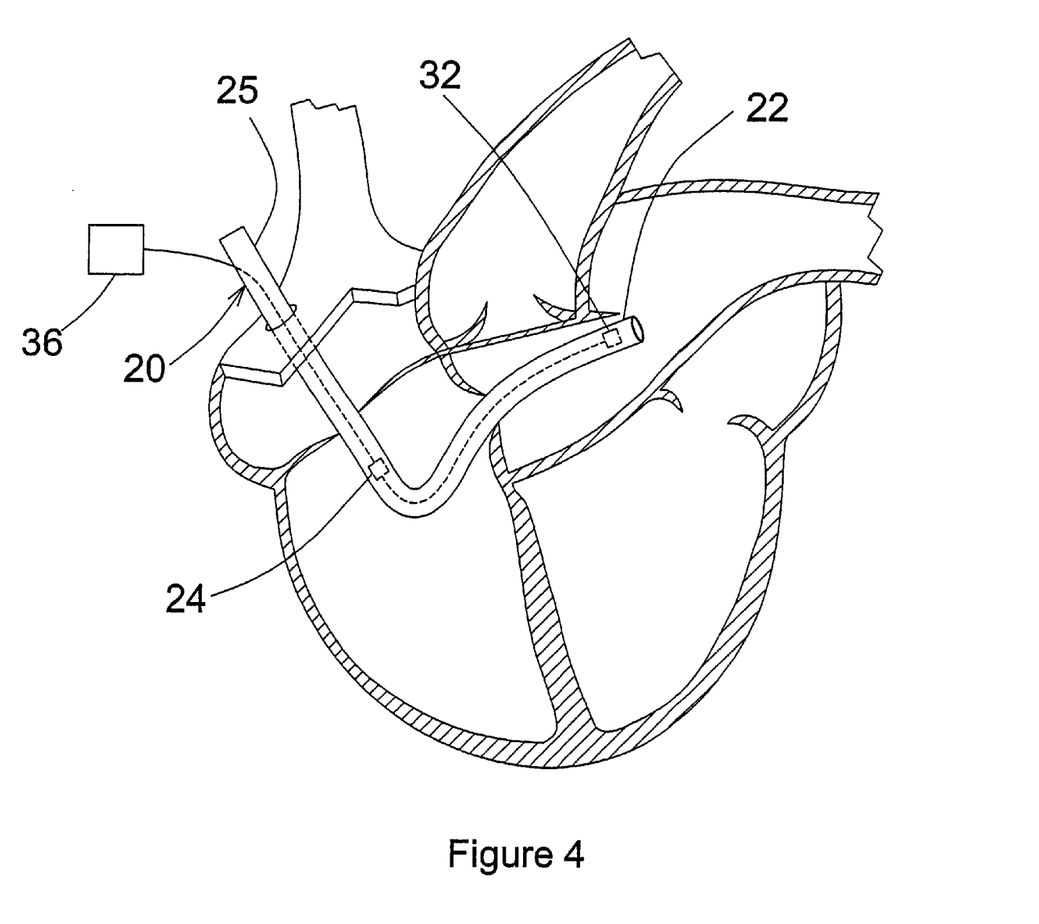
FIG. 4 is a schematic view of a cannula in accordance with the invention in a surgical application.

Pressure transducers 24, 32 are in electrical communication with console 36 via cable 38, which is supported in secondary lumen 42 provided in cannula 20. Calculations for determining fluid flow rate using signals generated by the pressure transducers 24, 32 and relayed via cable 38 are conducted at the console 36 or at any processor or processing system connected thereto.

Figure 5:
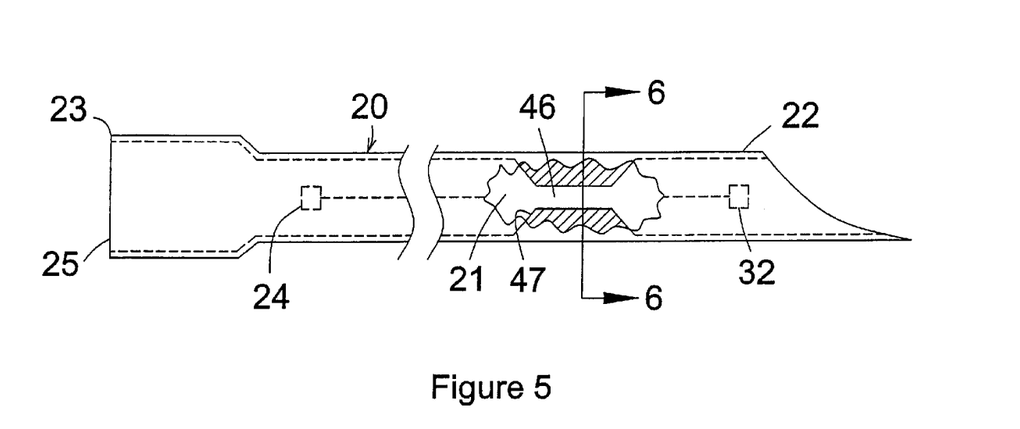
FIG. 5 is a schematic partial cut-away side view of a second embodiment of the invention.
Figure 6:
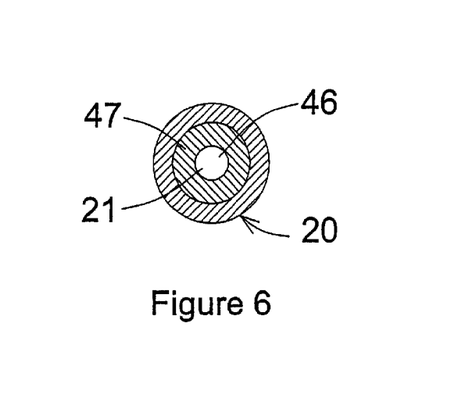
FIG. 6 is a schematic cross-sectional view taken along line 6—6 of FIG. 5.
Figure 19:
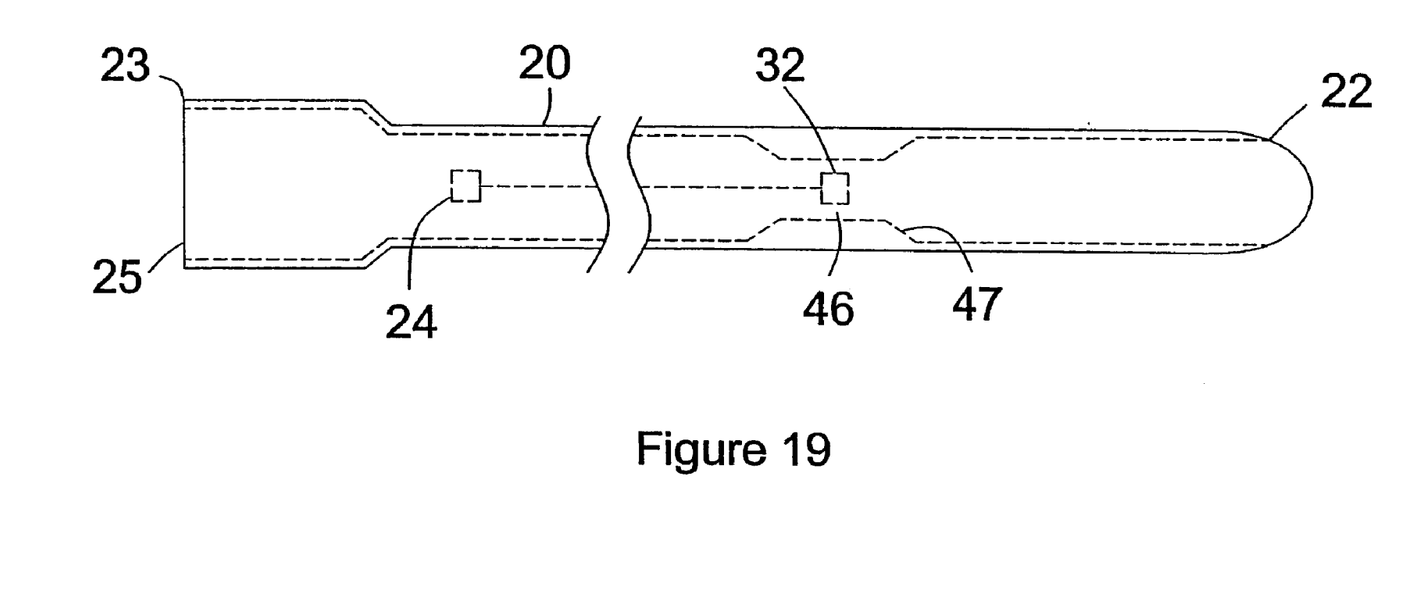
FIG. 19 is a schematic side view of an eleventh embodiment of the invention.

As shown in FIGS. 5 and 6, cannula 20 may also contain a partial occlusion portion 47 that forms a venturi 46 within the main lumen 21 of cannula 20. Venturi 46, which may be disposed anywhere along the length of the cannula 20, induces a pronounced pressure drop, creating a greater differential in pressure between proximal region 25 and distal region 22, thereby requiring less signal amplification of the pressure transducers and less filtering of the signal and consequently yielding a more accurate flow rate measurement. Preferably the location of the pressure transducer 32 is in the vicinity of venturi 46 as shown in FIG. 19.

Figure 7:
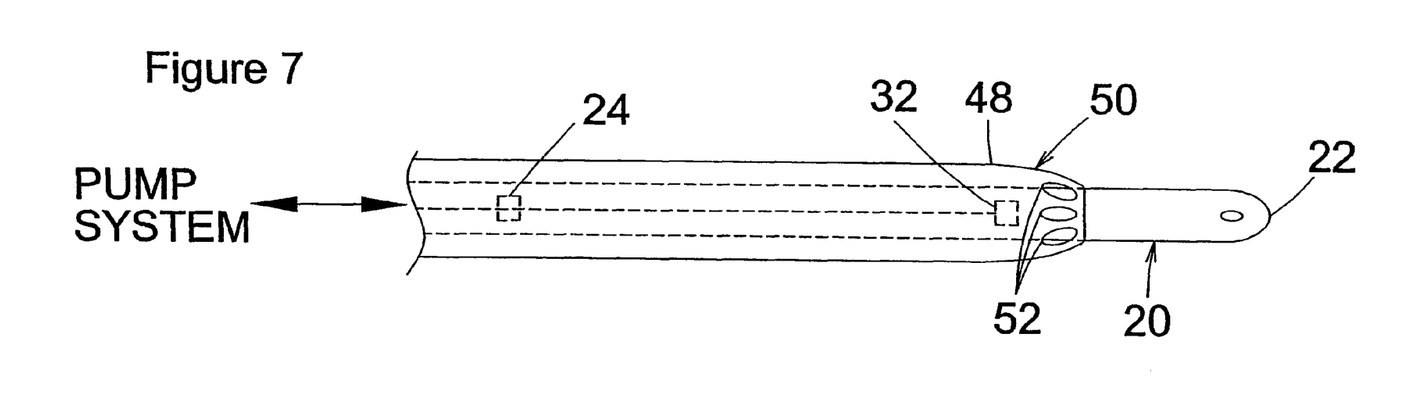
FIG. 7 is a schematic side view of a third embodiment of the invention.

FIG. 7 shows an embodiment in accordance with the invention in which the pressure transducers 24, 32 are used with a co-axial, single port device 50 in which cannula 20 is surrounded by a second, larger conduit 48, with cannula 20 for example operating to intake blood from the patient towards a pump system (not shown) and conduit 48 operating to replace the blood from the pump system, via openings 52, back into the patient for augmentation of blood flow during beating heart surgery as described in the co-pending PCT Application no. PCT/US97/18674 mentioned above. It is to be understood that pressure transducers 24, 32 can be mounted fixedly or detachably either to the interior or exterior of either the cannula 20 or the conduit 48 in the above-described manner. More than one pair of these transducers can also be used in a myriad possible combinations in accordance with the invention. In the preferred embodiment, the cannula 20 is provided with a bullet nosed tip, as illustrated in for example FIGS. 7–9. Other tip configurations, such as a bevel, may also be used, as will be appreciated by those skilled in the art.

Figure 8:
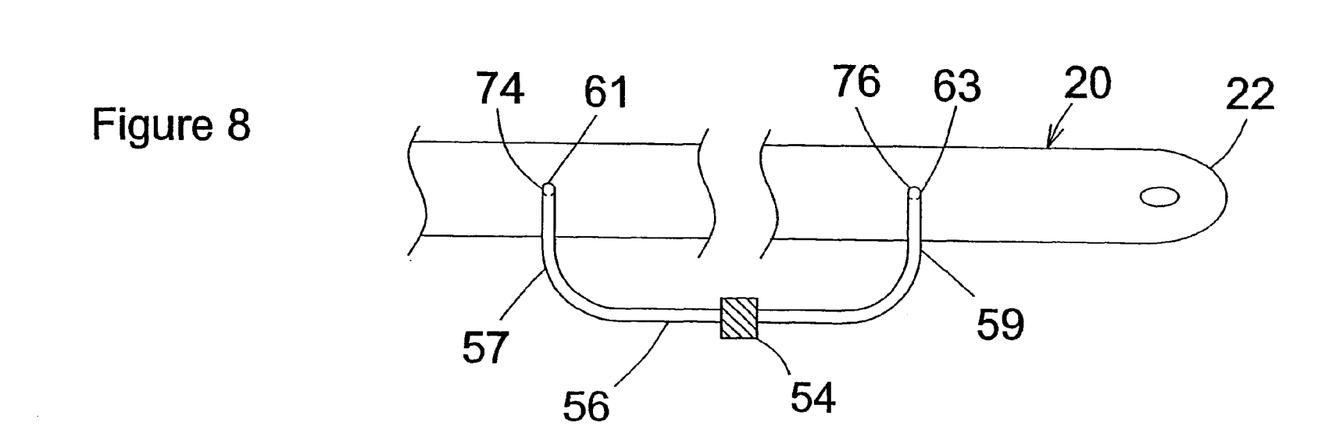
FIG. 8 is a schematic side view of a fourth embodiment of the invention.
Figure 9:
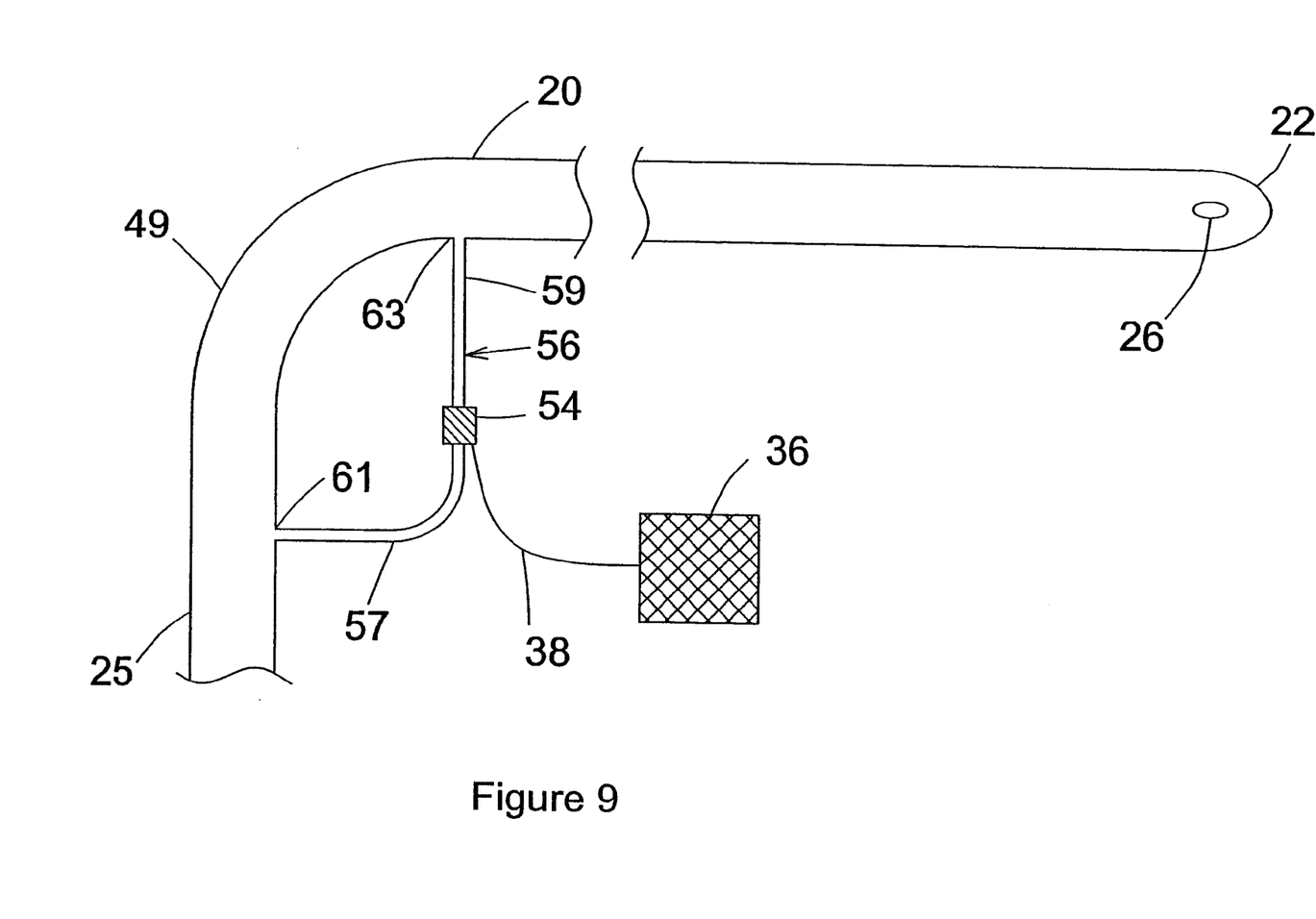
FIG. 9 is a schematic side view of a fifth embodiment of the invention.
Figure 10:
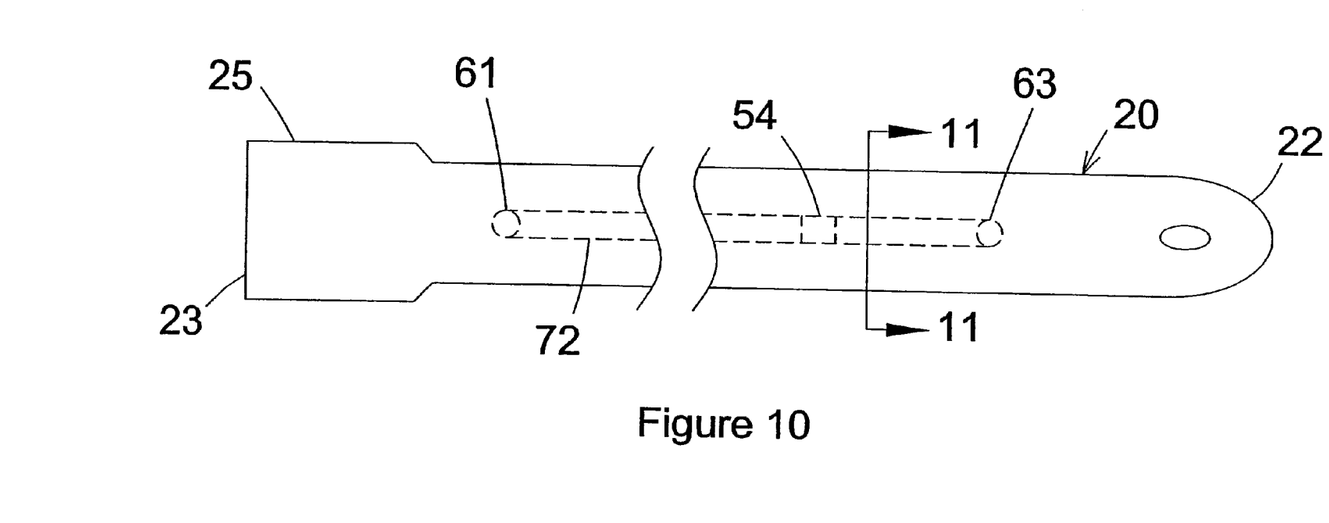
FIG. 10 is a schematic side view of a sixth embodiment of the invention.
Figure 11:
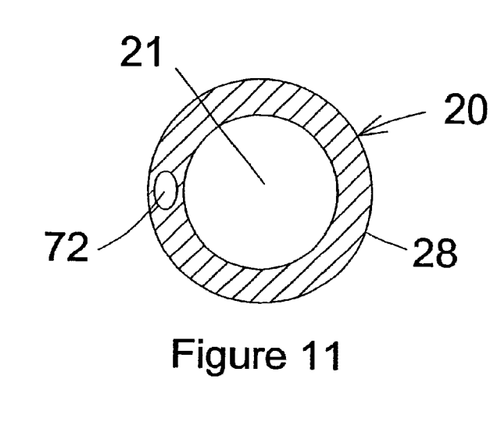
FIG. 11 is a schematic cross sectional view taken along line 11—11 of FIG. 10.

An alternative to using pairs of pressure transducers such as transducers 24, 32 is the use of a single differential pressure transducer 54, as shown in FIG. 8. Differential pressure transducers are also well known in the art and comprise for example a piezo-electric crystal electromechanically configured to be responsive to a pressure difference between two opposing sides thereof. These two sides correspond respectively to proximal end 57 and distal end 59 of secondary lumen 56 in which transducer 54 is mounted. Proximal and distal ends 57 and 59 are attached at any desired points along the length of cannula 20 to thereby couple secondary lumen 56 to main lumen 21 and provide a pressure difference measurement between the desired points. Attachment of lumen 57 and transducer 54 across knee 49 of cannula 20, as shown in FIG. 9, will provide a stronger signal, with knee 49 operating in accordance with the same principal as venturi 46 discussed above. Thus it is to be understood that a venturi could also be used in conjunction with the differential pressure transducer 54. The ports 61 and 63 at which the lumen 56 interfaces with cannula 20 may be sealed by an appropriate membrane, with saline or other fluid being permanently housed in the lumen 56. Alternatively, ports 61 and 63 may be open, permitting fluid communication between the cannula 20 and the lumen 56 and attached transducer 54. The latter, open configuration would achieve a more faithful pressure representation. Stopcocks 74 and 76 can be provided in the ports 61 and 63 to permit priming and/or de-airing of the ports. It should also be noted that although in the arrangements of FIGS. 8 and 9 the lumen 56 is provided as a separate tubular structure, lumen 56 may alternatively be formed integrally with wall 28 of cannula 20, again with ports 61 and 63 being either open or closed to main lumen 21 depending on the application. Such an arrangement is illustrated in FIGS. 10 and 11 in which is shown transducer 54 in communication with lumen 72 integrally formed in wall 28 of cannula 20.

Figure 12:
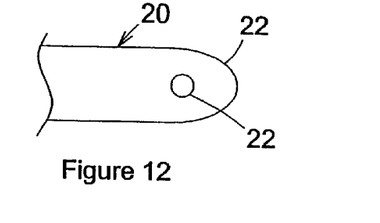
FIG. 12 is a schematic side view of a seventh embodiment of the invention.
Figure 13:
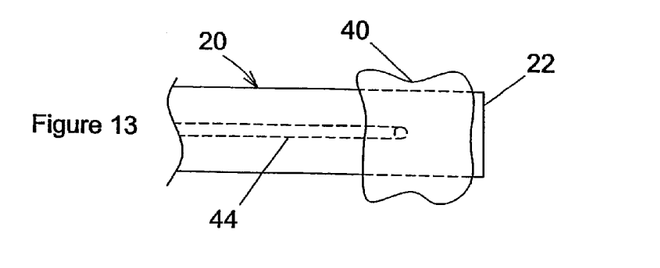
FIGS. 13 and 14 are schematic side views of an eighth embodiment of the invention.
Figures 14, 15:
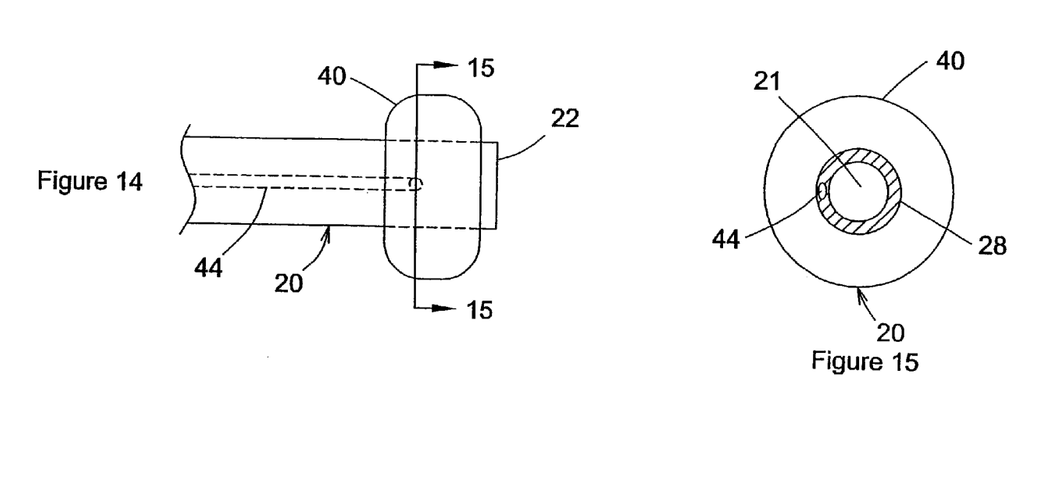
FIG. 15 is a schematic cross-sectional view taken along line 15—15 of FIG. 14.

Various distal tip configurations can be selected for cannula 20 and used with the pressure sensing transducers, depending on the particular application as appreciated by those of ordinary skill in the art. FIG. 12 shows an exemplary embodiment in which the distal tip 22 is formed of a soft, flexible material having a bullet shape. As shown exemplarily in FIGS. 13–15, the cannula 20 may be equipped to support other tools, such as an inflatable balloon 40 which is deployed for example in order to assist in transporting the distal tip 22 to the desired destination in the patient's body during the surgical procedure. Balloon 40 is inflated through an inflating lumen 44 provided in cannula 20 using a bio-compatible fluid such as saline or carbon dioxide gas. Preferably inflating lumen 44 is formed integrally within wall 28, by leaving an appropriate gap during the fabrication process, and is provided with a fitting (not shown) at its proximal end to interface with an inflating device for supplying the bio-compatible fluid. The lumen 21 within the cannula 20 can also be adapted to support a balloon catheter (not shown) which can be used to place the cannula within the patient's body. An obturator (not shown) may also be disposed through the main lumen 21 to aid in insertion and guiding within the patient's body.

Figure 16:
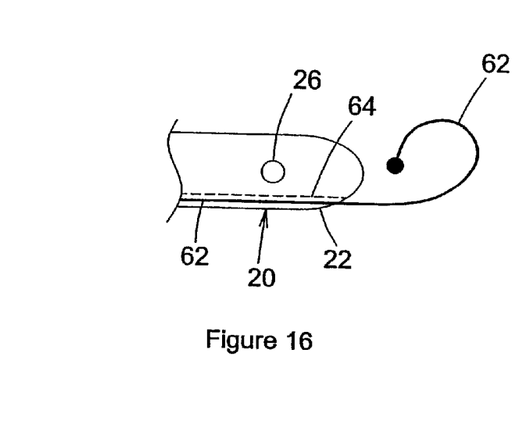
FIG. 16 schematic side view of a ninth embodiment of the invention.

Another tool which cannula 20 may support is shown in FIG. 16 and comprises a J-hook guidewire 62 disposed slidably within lumen 64, which is formed integrally in wall 28 of cannula 20. In operation, guidewire 62, easier to manipulate than the cannula 20, is first inserted into the patient's body and manipulated to the surgical site. Subsequently the cannula 20 is maneuvering along the guidewire 62, which passes through lumen 64, to the desired destination.

Figure 17:
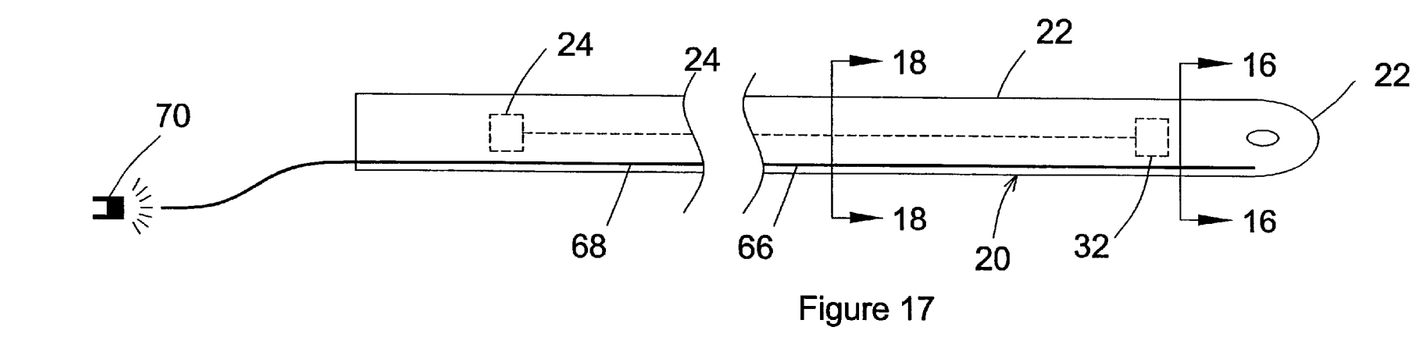
FIG. 17 is a schematic side view of a tenth embodiment of the invention.
Figure 18:
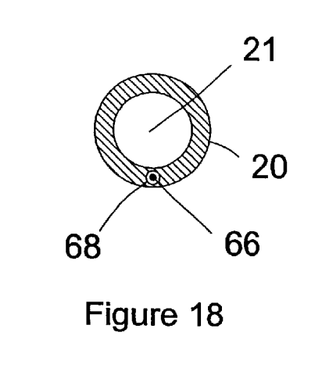
FIG. 18 is a schematic cross-sectional view taken along line 18—18 of FIG. 17.

As illustrated in FIGS. 17 and 18, cannula 20 may also contain a light guide 66, which may be supported in lumen 68. Light guide 66 comprises one or more optical fibers formed of for example glass or other materials, such as plastic, known for that purpose. Distal tip of light guide 66 is configured for light projection, such that light provided at the proximal end of light guide 66 is projected therefrom. An appropriate shape for such projection is a spherical shape, although other shapes and projection schemes, such as directional projection, fall within the purview of the invention. The source of light may be any conventional monochromatic (laser/LED) or polychromatic device 70, and more than one light source with associated light guide can be used for color coding and providing a visual reference to different portions of the cannula 20, depending on the colors of light used and on the location of the projection terminus of the light guides. In this manner cannula 20 can be visually guided through the patient's body, relying on the transmissivity of tissue to permit the location of the illuminated cannula in the patient's body. As will be appreciated, the location of the cannula 20 can also be determined by examining the pressure waveform detected by the pressure transducers 24, 32 and 54. The physiological pressure waveform recorded by the transducers can be used to determine the location of cannula 20 in relation to the valves of the patient's heart.

As will be appreciated by those skilled in the art, cannula 20 may be provided with one or more preformed curves along its length to aid in its manipulation through the patient's vasculature. Multiple curves may be disposed along the same plane or in different planes, depending on the application.

An additional feature in accordance with the invention is the use of radiopaque markings (not shown) anywhere along the cannula body. Such markings render portions of the cannula 20 visible to x-ray radiation for visualizing the cannula during its use.

The above are exemplary modes of carrying out the invention and are not intended to be limiting. It will be apparent to those skilled in the art that modifications thereto can be made without departure from the spirit and scope of the invention as set forth in the following claims. It will also be apparent that all devices and methods herein disclosed will adapt equally to animal use as well as human use.

What is claimed is:

1. A cannula assembly for use in surgical applications in a body, the cannula assembly comprising:

a substantially tubular structure formed of bio-compatible material and adapted for at least partial insertion into a body, said tubular structure having a wall defining a main lumen, said wall being of sufficiently rigid construction to prevent the collapse of said main lumen along at least a portion of said tubular structure; and at least one pressure transducer coupled to said non-collapsing portion of said tubular structure and adapted to measure pressure at a predetermined region in proximity of said wall.

2. The cannula assembly of claim 1, further comprising a processor for determining fluid flow rate using the measured pressure.

3. The cannula assembly of claim 2, wherein the fluid flow rate is representative of fluid flow within said main lumen.

4. The cannula assembly of claim 3, further comprising at least one conduit coupled to said non-collapsing portion of said tubular structure, said at least one conduit defining a secondary lumen communicatively coupled to said main lumen of said tubular structure, wherein said at least one pressure transducer comprises a differential pressure transducer communicatively coupled to said secondary lumen.

5. The cannula assembly of claim 4, wherein said secondary lumen is in fluid communication with said main lumen.

6. The cannula assembly of claim 4, wherein said secondary lumen contains fluid sealed therein.

7. A method of measuring pressure within a human body, comprising the steps of:

(a) providing a substantially tubular structure formed of a bio-compatible material and adapted for at least partial insertion into the body, said tubular structure having a wall defining a main lumen, said wall being of sufficiently rigid construction to prevent the collapse of said main lumen along at least a portion of said tubular structure; and (b) communicatively coupling at least one pressure transducer to said non-collapsing portion of said tubular structure to measure pressure at a predetermined region in proximity of said wall.

8. The method of claim 7, including the step (c) of providing a processor for determining fluid flow rate using the measured pressure.

9. The method of claim 8, wherein step (c) includes the further sub-step of determining the flow rate of the fluid flow within said main lumen.

10. The method of claim 9, including the step (d) of providing at least one conduit coupled to said non-collapsing portion of said tubular structure, said at least one conduit defining a secondary lumen communicatively coupled to said main lumen of said tubular structure; and wherein step (b) includes the further sub-step of communicatively coupling said at least one pressure transducer to said secondary lumen for determining the flow rate of the fluid flow within said main lumen.

11. The method of claim 10, wherein step (d) includes the further sub-step of providing said secondary lumen in fluid communication with said main lumen.

12. The method of claim 10, wherein step (d) includes the further sub-step of providing said secondary lumen containing fluid sealed therein.

* * * * *